United States Patent [19]

Cox et al.

[11] Patent Number: 5,079,155

[45] Date of Patent: * Jan. 7, 1992

[54] FLUOROCARBON POLYMER SUPPORT FOR CHROMATOGRAPHIC SEPARATIONS, DIAGNOSTIC ASSAYS AND ENZYME IMMOBILIZATION

[75] Inventors: Geoffrey B. Cox, Indianapolis, Ind.; Robert K. Kobos, Wilmington, Del.

[73] Assignee: E. I. du Pont de Nemours and Company, Wilmington, Del.

[*] Notice: The portion of the term of this patent subsequent to Dec. 5, 2006 has been disclaimed.

[21] Appl. No.: 413,867

[22] Filed: Sep. 28, 1989

Related U.S. Application Data

[63] Continuation-in-part of Ser. No. 134,028, Dec. 17, 1987, Pat. No. 4,954,444, which is a continuation-in-part of Ser. No. 20,808, Mar. 2, 1987, Pat. No. 4,885,250.

[51] Int. Cl.⁵ .............. C12N 11/06; G01N 33/549; C07K 3/20; C07K 17/06
[52] U.S. Cl. .............. 435/181; 435/7.92; 435/176; 435/180; 435/803; 436/524; 436/531; 436/532; 436/824; 530/412; 530/413; 530/416; 530/417; 530/811; 530/815; 530/816
[58] Field of Search .............. 435/7, 176, 180, 181, 435/182, 803, 815, 817, 7.92; 436/524, 528, 531, 532, 824; 530/811, 815, 816, 412, 413, 416, 417

[56] References Cited

U.S. PATENT DOCUMENTS

| | | | |
|---|---|---|---|
| 3,843,443 | 10/1974 | Fishman | 195/63 |
| 3,928,143 | 12/1975 | Coughlin | 435/176 X |
| 3,983,299 | 9/1976 | Regnier | 428/405 |
| 4,029,583 | 6/1977 | Chang et al. | 210/502 |
| 4,317,879 | 3/1982 | Busby et al. | 435/14 |
| 4,352,884 | 10/1982 | Nakashima et al. | 435/180 |
| 4,412,000 | 10/1983 | Lehmann et al. | 435/179 |
| 4,447,546 | 5/1984 | Hirschfeld | 436/527 |
| 4,508,832 | 4/1985 | Carter et al. | 436/517 |
| 4,600,646 | 7/1986 | Stout | 428/405 |
| 4,619,897 | 10/1986 | Hato et al. | 435/182 |
| 4,619,904 | 10/1986 | Giaever et al. | 436/518 |
| 4,735,906 | 4/1988 | Bastiaans | 436/527 |
| 4,885,250 | 12/1989 | Eveleigh et al. | 435/181 |

FOREIGN PATENT DOCUMENTS

0011504 7/1983 European Pat. Off. .

OTHER PUBLICATIONS

Danielson et al., Biotechnology and Bioengineering, 23, 1919–1917 (1981).
We et al., Methods in Enzymology, vol. XLIV: Immobilized Enzymes, Chap. 10, 134, Ed. K, Mosbach, Academic Press, New York (1976).
Varughese et al., Journal of Chromatographic Sciences, 26:401–405 (1988).
Berendsen et al., Anal. Chem., 52:1990–1993 (1980).
De Miguel et al., Chromatographia, 24:849–853 (1987).
Stout et al., Journal of Chromatography, 326:63–78 (1985).

Primary Examiner—David M. Naff
Attorney, Agent, or Firm—Roseanne R. Duffy

[57] ABSTRACT

A solid support useful for bioaffinity and ion-exchange separations and enzyme immobilization is provided. The support is based on a non-perfluorocarbon solid carrier core coated with a nonionic fluorosurfactant-coated fluorocarbon interlayer to which a ligand or a binder for the ligand is securely, but reversibly attached through a reactive perfluorocarbon anchor compound. Also provided is a solid support useful for size exclusion separations. Such support is based on a non-perfluorocarbon carrier core coated with a nonionic fluorosurfactant-coated fluorocarbon interlayer.

11 Claims, No Drawings

FLUOROCARBON POLYMER SUPPORT FOR CHROMATOGRAPHIC SEPARATIONS, DIAGNOSTIC ASSAYS AND ENZYME IMMOBILIZATION

CROSS-REFERENCE TO RELATED APPLICATIONS

This application is a continuation-in-part of application Ser. No. 07/134,028, filed Dec. 17, 1987, now U.S. Pat. No. 4,954,444 which, in turn, is a continuation-in-part of application Ser. No. 07/020,808, filed Mar. 2, 1987, now U.S. Pat. No. 4,885,250.

TECHNICAL FIELD

This invention is related to solid supports for use in the separation of biomolecules, heterogeneous diagnostic assays, enzyme immobilization and biosensors and, more specifically, to a method of surface modification of solid carriers, fluorosurfactant treatment of such surface-modified solid carriers and their application for such uses.

BACKGROUND ART

Separation of biomolecules can be achieved by affinity reactions employing the specific binding of a biomolecule with its binding partner immobilized on a solid carrier. Bioaffinity separation is defined as an affinity separation in which one of the components involved in the affinity reaction is biologically active or is of biological interest. Bioaffinity separations generally involve at least one biomacromolecule, such as a protein or nucleic acid, as one of the components of the binding pair. Examples of such bioaffinity binding pairs include: antigen-antibody, substrate-enzyme, effector-enzyme, inhibitor-enzyme, complementary nucleic acid strands, binding protein-vitamin, binding protein-nucleic acid; reactive dye-protein, reactive dye-nucleic acid; and others. The terms ligand and its binding partner for the ligand or, simply, binder will be used to represent the two components in specific bioaffintiy binding pairs.

Affinity separations are generally considered to require the use of solid carriers derivatized with a ligand or binder. These separations can be carried out as batch processes or chromatographic processes with the latter generally being preferred. Affinity chromatography is well known and has been reviewed, for example, in C. R. Lowe, "An Introduction to Affintiy Chromatography", North Holland Publishing Company, Amsterdam, New York, 1978. Lowe describes the characteristics desirable in a solid carrier to be used in an affinity separation. According to Lowe, the solid carrier should form a loose, porous network to allow uniform and unimpaired entry and exit of large molecules and to provide a large surface area for immobilization of the ligand; it should be chemically inert and physically and chemically stable; and the carrier must be capable of functionalization to allow subsequent stable coupling of the ligand. Additionally, the particles should be uniform, spherical and rigid to ensure good fluid flow characteristics.

The list of support materials suitable for affinity chromatrography is extensive and will not be reviewed here (see Lowe, 1978, for a partial listing). It is not generally possible for a given support to achieve all of the above objectives. One requirement faced in preparing affinity supports from any carrier is the efficient and stable attachment of the ligand or binder to the carrier. The most common method employed is covalent attachment generally by modification of the carrier surface with a reactive reagent which then covalently bonds to the ligand or binder. Representative examples of this approach are given by Weetal, Methods in Enzymology, Volume XLIV: Immobilized Enzymes, Chapter 10, page 134, Ed. K. Mosbach, Academic Press, New York, 1976. The major disadvantages of this approach has been as follows: modification of the surface properties of the carrier which frequently results in increased nonspecific binding of unwanted proteins; inactivation of a significant portion of ligands or binders being bound; and the permanence of the attachment preventing recovery of scarce or expensive ligand or binder.

Another attachment method is the modification of ligand or binder to effect a specific interaction between the ligand or binder and the carrier. Applicants' assignee's, E.I. du Pont de Nemours & Company, copending applications, Ser. Nos. 07/134,028, filed Dec. 17, 1987, and 07/020,808, filed Mar. 2, 1987, disclose solid perfluorocarbon polymer-based affinity supports prepared by attaching a perfluorocarbon-substituted ligand or binder to a perfluorocarbon polymer carrier and coating the resulting carrier having the attached perfluorocarbon-substituted ligand or binder thereon with a nonionic fluorosurfactant to reduce nonspecific binding. Although this approach has many advantages over the conventional covalent attachment method, it is limited to perfluorocarbon-polymer based carriers.

Berendsen et al., Anal. Chem., Vol. 52, 1990-1993, 1980, describe enhanced retention of fluorine-containing compounds on fluorocarbon bonded phases in liquid chromatography.

De Miguel et al., Chromatographia, Vol. 24, 849-853, 1987, describe the strong retention of phenyl-D-glucopyranoside modified with multiple fluorocarbon chains on fluorocarbon bonded phases under reversed phase conditions. The authors speculate that such strong retention can allow dynamic anchoring of biomolecules. However, no examples or discussions of nonspecific binding problems were provided.

Size exclusion chromatography, often referred to as gel filtration chromatography, has also been widely used in the separation of biomolecules due to simplicity of the technique, and has been reviewed extensively, for example, by Yau et al., in "Modern Size Exclusion Liquid Chromatography". Separations are achieved based on the molecular weight, size, or shape of the biomolecules. While most affinity separation techniques utilize relatively nonporous or loosely crosslinked solid carriers, size exclusion chromatography employs porous supports of a controlled pore size to effect the separation. Until recently, the porous supports were agarose-based gels which lacked rigidity and chemical resistance such as to changes in pH or ionic strength [Chang et al., U.S. Pat. No. 4,029,583, issued June 14, 1977]. The agarose-based gels have been replaced by silica gels which are rigid and inexpensive. However, use of such rigid supports has been impaired by the problems of nonspecific binding and denaturation of biomolecules following adsorption.

U.S. Pat. No. 3,983,299, issued Sept. 28, 1976 to Regnier, discloses a method of treating the surface of silica with ligands containing carbohydrate-like moieties to overcome nonspecific binding problems. However, silica gel packings made by this procedure are not hydrolytically stable, especially at pH values above 7.

U.S. Pat. No. 4,600,646, issued July 15, 1986 to Stout, discloses a method of silica surface stabilization by treatment of such surface with metal oxides such as zirconium oxide. Although the stability of silica surfaces and that of the attached ligands are much improved, the problem of nonspecific binding is not fully solved. For example, lysozyme, a highly negatively charged protein, is retained by the stabilized surface. In fact, lysozyme is used to detect nonspecific adsorption problems [column 9, lines 19–45].

The supports described in copending applications, Ser. Nos. 07/134,028 and 07/020,808, are of little value in size exclusion chromatography because of the non-porous nature of the perfluorocarbon polymer carriers.

Biosensors utilize various transducers onto which biomolecules are attached as means for detection. For example, the transducer can be an electrode, semiconductor sensor, fiber optic sensor, piezoelectric sensor or thermistor capable of converting biochemical activity to a measurable signal. The piezoelectric sensor can be a bulk AT-cut quartz crystal or a quartz surface acoustic wave (SAW) device. The biological substance immobilized on the surface of the transducer can be an enzyme, intact cell, antigen, or antibody. Many examples of biosensors are given by Turner et al., "Biosensors: Fundamentals and Applications", Oxford University Press, Oxford, 1987, Borman, Anal. Chem., Vol. 59, 1091A–1098A and 1161A–1163A, 1987, and Thompson et al., Trends Anal. Chem., Vol. 3, 173–177, 1984.

Biosensors employing a specific binding interaction such as those involving antigen-antibody, complementary nucleic acids or their fragments, and chemoreceptor-stimulant have utility in many clinical applications. The detection in these sensors is based on the known methods of enzyme immunoassay (EIA), fluorescence immunoassay (FIA) or the direct measurement of a signal resulting from the binding interaction. Several approaches to immunosensors have been reviewed by North, Trends Biotechnol., Vol. 3, 180–186, 1985. Similarly, Herschfeld, U.S. Pat. No. 4,447,546, issued May 8, 1984, describes a method of detecting a fluorescence label using a fiber optic sensor.

U.S. Pat. No. 4,508,832, issued Apr. 2, 1985 to Carter et el., discloses a bioassay method for determining a bioactive substance in a sample by the reaction of the bioactive substance with it binding partner. The method utilizes an optical immunosensor comprising a layer of antigen or antibody immobilized on the surface of a transparent, dielectric plate. The rate of optical change at the interface of said plate surface and the immobilized layer, resulting from the specific binding reaction in the reaction vessel, is then measured ellipsometrically. Detection is based on the measurement of a phase shift of the reflected polarized light due to the binding reaction. Detection requires the use of an ellipsometer equipped with a complex optical system to provide a polarized incident light at a defined angle and a detection means for measuring the phase shift of the polarized light. Thus, although the method obviates the need to label a reagent, it requires a sophisticated detection system.

U.S. Pat. No. 4,735,906, issued Apr. 15, 1988 to Bastiaans et al., discloses an immunosensor using surface acoustic waves on a piezoelectric quartz crystal. An antibody is immobilized onto the quartz surface using commonly available organosilane coupling reagents. The signal measured is a shift in the resonance frequency of the crystal induced by the surface mass change that occurs as the binding reaction takes place. This technique also offers direct measurement capability but the detection sensitivity is limited by nonspecific adsorption problems.

There is a need for solid supports, and a general method of preparing them, to suit the specific needs of various applications which have secure but reversible attachment of a ligand and or binder for the ligand to a carrier and have reduced nonspecific binding, yet retain desirable properties of the carrier, such as porosity.

SUMMARY OF THE INVENTION

The solid support of this invention useful for bioaffinity and ion-exchange separations and enzyme immobilization consists essentially of a non-perfluorocarbon solid carrier core; a fluorocarbgn interlayer coated on the solid carrier core; a ligand or binder securely but reversibly attached to the surface of the fluorocarbon interlayer through a reactive perfluorocarbon anchor compound; and a nonionic fluorosurfactant coating on the fluorocarbon interlayer.

The solid support of this invention useful for size exclusion separations which consists essentially of a non-perfluorocarbon solid carrier core; a fluorocarbon interlayer coated on the solid carrier core; and a nonionic fluorsurfactant coating on the fluorocarbon interlayer.

DESCRIPTION OF THE INVENTION

Advantages of the perfluorocarbon polymer-based solid supports disclosed in copending applications, Ser. Nos. 07/134,028 and 07/020,808, include: recoverability of scarce or expensive ligand or binder for the ligand; attachment of ligand or binder for the ligand with known activity; stability in an aqueous environment; amenability to treatment to achieve low nonspecific binding to native proteins; and inertness and rigidity of the perfluorocarbon polymer-based solid carrier.

The solid support of this invention offers additional advantages over the perfluorocarbon polymer-based supports in carrying out chromatographic separations, diagnostic assays, and enzyme immobilization. While the rigid and non-porous nature of the perfluorocarbon polymer carrier is advantageous in most affinity separation applications, it is of limited value in other applications such as size exclusion or ion-exchange chromatographic separations. The greatest advantage of this invention is the ability to use any desired solid carrier core, i.e., non-perfluorocarbon polymer-based solid carrier, to generate a solid support to suit the specific needs of various applications.

The solid supports of this invention for use in bioaffinity separations and enzyme immobilization contain a non-perfluorocarbon solid carrier core, a fluorocarbon interlayer coated on the core, a ligand or binder securely but reversibly attached to the fluorocarbon interlayer through a reactive perfluorocarbon anchor compound, and a nonionic fluorosurfactant coating on the fluorocarbon interlayer. By perfluorocarbon is meant a moiety which contains the largest possible or a relatively large proportion of fluorine atoms in its structure.

The non-perfluorocarbon solid carrier cores suitable for preparing the supports of this invention include inorganic substances such as silica, magnetic particles, and polymers such as polystyrene, polypropylene and polyethylene. The surface of these carriers can contain reactive groups and can be in any form or shape, such as wells of a microtiter plate, tubes or beads. The solid carriers can also be porous or nonporous. A preferred carrier core of this invention is porous silica.

By fluorocarbon interlayer is meant a layer of fluorocarbon compound coating the surface of the non-perfluorocarbon solid carrier core. The fluorocarbon compound can be a fluoropolymer, fluorosilane or other substances containing a highly fluorinated hydrocarbon chain and which, optionally, can have a reactive group capable of reacting with the surface of the solid carrier core.

By ligand is meant an antigen, hapten, nucleic acid, enzyme substrate, vitamin, dye or other small organic molecule including enzyme substrates, effectors and inhibitors and by binder is meant an antibody, enzyme, nucleic acid, binding protein, synthetic mimics of binding proteins such as polylysine and polyehtyleneimines or other biomacromolecule capable of specific binding, enzyme-substrate, etc. interactions.

By reactive perfluorocarbon anchor compound is meant a moiety containing, at one end, an anchor portion capable of attaching to the fluorocarbon interlayer and, at the other end, a reactive group capable of reacting with the ligand or binder for the ligand. The anchor portion and the reactive group can be separated by a spacer group.

By nonionic fluorosurfactant is meant a surfactant containing a highly fluorinated anchor group, such as Zonyl® FSN fluorosurfactant, (a registered trademark of E. I. du Pont de Nemours & Company), and compounds having the formula $C_nF_{2n+1}CH_2CH_2(OCH_2CH_2)_mOH$ where n is an integer greater than 4, preferably 6-10, and m is an integer greater than 6, preferably 9-15.

A general method of forming the solid support of this invention useful for bioaffinity separations and enzyme immobilization is to form a fluorocarbon interlayer by coating a fluorocarbon compound on a non-perfluorocarbon solid carrier core; attaching a ligand or binder for the ligand to the fluorocarbon interlayer through a reactive perfluorocarbon anchor compound; and coating the fluorocarbon interlayer having the attached ligand or binder for the ligand with a nonionic fluorosurfactant.

Several approaches can be used to form the fluorocarbon interlayer on the solid carrier. For example, the non-fluorocarbon surface of the carrier can be spray coated with a solution of soluble fluoropolymer, such as polyvinylidene difluoride, in organic solvent, such as methyl ethyl ketone. Alternatively, the interlayer can be introduced in a batch process by soaking the carrier in a solution containing the dissolved fluoropolymer. Yet another approach is to coat the surface of the carrier with high density polyethylenefirst then fluorinating the polyethylene by passing a fluorine gas mixture in nitrogen gas over the surface.

When the carrier is silica, fluoroalkylsilanes having chloro-or alkoxy-groups, such as heptadecafluoro-1,1,2,2- tetrahydrodecyldichloromethyl silane, can be used under non-aqueous conditions.

The surface of virtually any substance can be converted into a fluorocarbon surface through the interlayer. In all cases, however, the optimal conditions must be experimentally determined to achieve the desired thickness of the fluorocarbon interlayer. The surface of the solid carrier core needs sufficient coverage with the fluorocarbon interlayer for secure subsequent attachment of ligand or binder for the ligand.

The supports of this invention must have the ligand or binder securely attached to the fluorocarbon interlayer. By secure attachment is meant an attachment capable of surviving the steps involved in the use of the solid supports of this invention such as in bioaffinity separations. However, this attachment needs to be reversible when desired, for example, when desiring to regenerate the carrier, such as by displacement of ligand or binder by chaotropic agents. Secure attachment is necessary so that ligand or binder does not contaminate purified product and also to prevent loss of capacity of the support. With prior supports, secure attachment is usually accomplished by covalently attaching the ligand or binder to the support. In addition to attaching ligand or binder securely, it is desirable not to alter the general inertness of the carrier nor to introduce functional groups which might increase nonspecific binding. Further, it is desirable to develop general methods which can be applicable to a variety of ligands or binders.

The preferred method of attaching ligand or binder to the fluorocarbon interlayer is referred to as the partition or adsorption method. In this method, the ligand or binder is modified to permit its selective high affinity (secure) binding to the fluorocarbon interlayer. One means to accomplish this is to prepare and purify a highly or perfluorocarbon-substituted ligand or binder prior to attachment to the fluorocarbon interlayer. The perfluorocarbon groups attached to the ligand or binder are called reactive perfluorocarbon anchor compounds. Several well known chemical strategies can be used to attach covalently highly fluorinated groups to ligands or binders. Factors which should be considered are reactivity of the fluorinated compound used, the pH of the reaction medium, and the time and temperature of the reaction.

Compounds such as the acid chlorides, anhydrides and imidazolides of various perfluorocarbon acids, for example, perfluoroctanoyl chloride, perfluorocotyl acetyl and propanoyl chlorides and perfluorooctanoyl and perflurooctyl propanoyl imidazolides can be used successfully during the preparation of the solid supports of this invention. The preferred compounds are highly fluorinated isocyanates having the formula, $RFCH_2CH_2CH_2NCO$, wherein $R_F$ can be a linear, branched or carbocyclic perfluorinated radical containing 1-20 carbon atoms. In a preferred class of the above compounds, $R_F$ is a linear $F(CF_2)_n$ radical. A more specifically preferred compound is perflurooctylpropyl isocyanate, $F(CF_2)_8CH_2CH_2CH_2NCO$.

The isocyanates are most preferred because of their increased stability to hydrolysis at the slightly alkaline reaction conditions generally used during the preparation of the fluorocarbon-substituted ligand or binder. In addition, the small amount of hydrolysis products formed (amines and ureas) do not interfere with the adsorption of the modified ligand or binder to the fluorocarbon interlayer. This eliminates the need to purify the modified ligand or binder from the reaction milieu in which it was prepared prior to forming the solid affinity support of this invention.

In general, the modification reactions are carried out by mixing an aqueous solution of the ligand or binder with the fluorinated reagent dissolved in a water miscible organic solvent such as tetrahydrofuran or acetonitrile under controlled time, temperature and pH conditions. The modified ligand or binder can be separated from the by-products of the reaction and the organic solvent by gel filtration or dialysis. The degree of substitution can be determined by any of the known techniques such as trinitrobenzene sulfonate labeling.

The degree of substitution required to provide secure attachment of the ligand or binder to the fluorocarbon interlayer is expected to vary significantly depending on the nature of the reactive perflorocarbon anchor compound, the spatial arrangement of the anchor groups on the ligand or binder, the size and nature of the ligand or binder, and the eventual use of the support. In general, the higher the degree of substitution the stronger the attachment. The degree of substitution, however, can be limited by steric considerations as well as the need to retain the biological activity of the ligand or binder. When the ligand is a protein, it has been found that placing reactive perfluorocarbon anchor compounds on approximately 20% of the available amino groups is preferred. The fluorocarbon-substituted ligand or binder is now ready to be used to form the affinity support of this invention.

The affinity support can be formed by contacting the fluorocarbon interlayer-coated carrier with a buffered solution of the above perfluorocarbon-substituted ligand or binder. It is advantageous to prime the surface of the interlayer with an organic solvent such as methanol or t-butanol prior to contacting with the buffered solution. The solvent treatment can improve the wettability of the interlayer and can result in faster and more efficient immobilization. Immobilization can be effected by stirring a suspension of the wetted fluorocarbon interlayer-coated carrier in a solution containing a perfluorocarbon-substituted ligand or binder, in a process referred to as a batch process. Alternatively, the immobilization can be effected by a chromatographic process involving a column packed with the wetted fluorocarbon interlayer-coated carrier. Batch processes generally give higher levels of attachment than chromatographic processes.

While the fluorocarbons used to prepare the fluorcarbon interlayer are inert and display low nonspecific binding characteristics, some nonspecific binding can occur. The nonspecific binding of these fluorocarbon interlayers can be further decreased by coating them with nonionic fluorosurfactants such as Zonyl ® FSN. The fluorosurfactant appears to coat the surface of the fluorocarbon interlayer preventing binding of other materials. These fluorosurfactants can also prevent the binding of the modified ligands or binders and, therefore, the coating of the fluorocarbon interlayer-coated carrier core is preferably carried out after the perfluorocarbon-substituted ligand or binder is attached to the fluorocarbon interlayer-coated carrier core. The fluorosurfactants will not, however, cause the release of the perfluorocarbon-substituted ligands or binders from the fluorocarbon interlayer-coated carrier core.

Either batch or dynamic loading processes can be utilized to add the nonionic fluorosurfactant. The optimal reaction condition will depend on the nature of the fluorocarbon interlayer, reactive perfluorocarbon anchor compound, ligand or binder, surfactant composition, and eventual use of the support. As an example, a solution of 0.05 to 2.5% w/v Zonyl ® FSN, preferably 0.2%, in water, can be added to block all exposed surfaces of the fluorocarbon interlayer.

A second method for attaching ligands or binders to a fluorocarbon interlayer-coated carrier core is referred to as the direct method. In this method, a non-perfluorocarbon solid carrier core coated with a fluorocarbon interlayer to which a reactive perfluorocarbon anchor compound is attached is contacted with unmodified ligand or binder to attach the ligand or binder to the fluorocarbon interlayer through the reactive portion of the anchor compound.

In this method, the fluorocarbon interlayer-coated carrier core is preactivated with a reactive perfluorocarbon anchor compound to introduce onto the surface of the fluorocarbon interlayer groups which are capable of reacting with ligand or binder. Unmodified ligand or binder is contacted with the preactivated fluorocarbon interlayer-coated carrier core resulting in the attachment of the ligand or binder through the reactive groups of the reactive perfluorocarbon anchor compound.

A major disadvantage of other methods for preactivating carrier surfaces is the inactivation of a significant number of the ligands or binders being attached. Surprisingly, however, the direct method of this invention has been found to be highly useful for immobilization of those enzymes which are often denatured upon adsorption to strongly hydrophobic fluorocarbon interlayers. Another important advantage of the direct method is that the attached enzymes are still recoverable since the anchor groups are reversibly attached to the interlayer.

The direct method is also advantageous in that a spacer group can be introduced between the anchor portion and the reactive group of the reactive perfluorocarbon anchor compound. The addition of a spacer group can result in even higher retention of biological activity of ligand or binder. Spacers suitable for this purpose can be derived from polylysine, polyglutamic hydrazide, polyacrylic hydrazide, hexamethylene diamine and 6-aminocaproic acid. Hydrophilic spacers containing ethylene glycol, such as ethylene glycol bis(3-aminopropylether) and diethylene glycol bis(3-aminopropylether), are preferred.

Modified reactive perfluorocarbon anchor compounds containing additional spacer groups can be prepared by reacting the reactive perfluorocarbon anchor compound with a spacer group in an organic solvent, such as dioxane or acetonitrile. For example, under proper reaction conditions, perfluorooctylpropyl isocyanate can be reacted with either ethylene glycol bis(3-aminopropylether) or diethylene glycol bis(3-aminopropylether) in dioxane and perfluorooctylpropyl amine or perfluorohexylpropyl amine can be reacted with either ethylene glycol bis(succinimidylsuccinate) or 1,4-butanediol diglycidyl ether in dioxane. A partially aqueous solution containing the modified reactive perfluorocarbon anchor compound, for example, 10–50% organic solvent, can then be added to the wetted surface of the fluorocarbon interlayer.

The affinity support can then be prepared by adding a solution of unmodified ligands or binders to a preactivated material. Any excess free reactive groups can be inactivated by hydrolysis or can be blocked chemically.

Where the spacer group is hydrophilic, e.g., that derived from ethylene glycol, the modified reactive perfluorocarbon anchor compound can act as a fluorosurfactant to minimize nonspecific binding. The fluorocarbon interlayer can be substantially completely coated with a modified reactive perfluorocarbon anchor compound, making further fluorosurfactant coating after the immobilization of ligand or binder unnecessary. However, the activity of some ligands or binders can be adversely affected by completely coating the fluorocarbon interlayer with such a modified reactive perfluorocarbon anchor compound. Therefore, partial coverage of the fluorocarbon interlayer with modified reactive perfluorocarbon anchor compound, followed by protein immobilization and fluorosurfactant coating of the fluorocarbon interlayer, is preferred.

The direct method can also be useful for preparing enzyme biosensors where maximal retention of the activity of the ligand or binder for the ligand is especially important due to the limited surface area available on the transducer. Many transducers for biosensors have silica surfaces which can be modified to create a fluorocarbon interlayer. For example, the surface of a piezoelectric quartz crystal can be reacted with a fluoroalkylsilane, such as heptadecafluoro-1,1,2,2,-tetrahydrodecyldichloromethyl silane. Then, the fluorocarbon interlayer can be preactivated with a reactive perfluorocarbon anchor compound. Subsequently, a ligand or binder for the ligand can be attached to the fluorocarbon interlayer through the reactive group of the reactive perfluorocarbon anchor compound to form a biosensor. Similarly, silica core optical fibers or wave guides, silicon semiconductors, and surface acoustic wave (SAW) devices can also be modified with fluorosilane.

The affinity support of this invention can be used in other applications as well. Examples include the use in extracorporeal blood depletion therapy; nucleic acid hybridization assay to capture complementary DNA or RNA from a reaction mixture; and various configurations of solid phase specific binding assays, including immunoassays.

Within the scope of this invention, the ligand can be a hapten. The hapten can be a nonionic surfactant head group which can then be modified to attach a highly fluorinated anchor group, forming a nonionic fluorosurfactant. Therefore, the perfluoroalkylated ligand of the instant invention can also be the fluorosurfactant of the instant invention. A support utilizing such a hapten is useful for size exclusion chromatographic separations. Similarly, the hapten can be a cationic surfactant head group which can then be modified to attach a highly fluorinated anchor group, forming a cationic fluorosurfactant, such as Zonyl® FSC fluorosurfactant, a fluorosurfactant containing a quaternary ammonium salt. A support utilizing such a cationic hapten is useful for ion-exchange chromatographic separations.

A preferred non-perfluorocarbon solid carrier core for size exclusion and ion-exchange chromatography is porous silica. Porous silica particles are rigid, capable of withstanding the high pressures which allow separations of biomolecules in very short times. The small size particles also provide high efficiency columns for difficult separations because of the large number of theoretical plates. Furthermore, the silica particles can provide a range of controlled porosities that accomodate separations of biomolecules in a wide range of molecular weights.

The silica gel particles prepared by the procedure described in U.S. Pat. No. 3,855,172 to Iler et al., incorporated herein by reference, are particularly preferred for preparing the supports of the instant invention useful for size exclusion and ion exchange chromatography. Such silica gel particles can be stabilized by the method described in U.S. Pat. No. 4,600,646 to Stout, incorporated herein by reference. The stabilized silica particles can then be treated with fluoroalklylsilanes to attach a fluorocarbon interlayer. The preferred method for attaching a fluorocarbon interlayer is to prepare a bonded phase silica by reacting the stabilized silica particle surface with heptadecafluoro-1,1,2,2,tetrahydrodecyldichloromethyl silane under non-aqueous conditions using a catalyst such as an amine. A preferred solvent for use in such reaction is a mixture of toluene and dimethylformamide and a preferred catalyst is imidazole.

For size exclusion and ion-exchange chromatography, it is essential that nonspecific binding be controlled to prevent retention of substances which can contaminate the purified product. Perfluorocarbon-based packing materials are known to exhibit severe non-specific binding under normal separation conditions. For the size exclusion and ion-exchange supports of the instant invention, such non-specific binding can be substantially eliminated by coating the surface of the fluorocarbon interlayer with a hydrophilic, nonionic fluorosurfactant. For the size exclusion support of this invention, the perfluoroalkylated ligand, which is a perfluoroalkylated surfactant head group as described above, can act as the flurosurfactant to reduce non-specific binding.

The following Examples describe the invention.

EXAMPLE 1

Preparation of a Porous Silica-Based Support and Its Use in Size Exclusion Chromatography

A. Preparation of Fluorosurfactant-Treated Fluorosilane-Coated Porous Silica-Based Support Fifty grams of silica gel (Zorbax™ PSM 300) coated with zirconium oxide by the procedure as described in U.S. Pat. No. 4,600,646 to Stout, incorporated herein by reference, were heated and stirred in a mixture of 350 mL of toluene and 40 mL of dimethylformamide (DMF) containing 57 g imidazole under a Dean-Stark trap. A 50-mL fraction of the distillate was removed and the residual silica mixture was allowed to cool to approximately 50° C. To attach a fluorosilane interlayer onto the silica, the Dean-Stark trap was removed and 80 g of heptadecafluoro-1,1,2,2- tetrahydrodecyldichloromethyl silane (HDF-silane) was added to the silica mixture. The silica-HDF-silane mixture was refluxed for two hours, cooled and filtered. The HDF-silane-coated silica was then washed with 80% aqueous tetrahydrofuran (THF), resuspended in 350 mL of 80% aqueous THF and refluxed for 5 minutes. The HDF-silane-coated silica was cooled to 50° C., filtered and twice washed with 200 mL of THF per wash. The coated silica was resuspended in 350 mL of 80% aqueous THF, refluxed for 10 minutes, filtered, twice washed with 200 mL of THF per wash and twice washed with 200 mL of Freon® TF per wash. The resulting coated silica was dried first in air and finally in a vacuum oven at 110° C.

To coat the HDF-silane-coated silica with fluorosurfactant, the coated silica was packed into a 25×0.94 cm chromatographic column and flushed with water. A solution of 0.5% Zonyl® FSN in water was pumped through the column at a flow rate of 0.5 mL/min.

B. Use of a Fluorosurfactant-Treated Fluorosilane-Coated Porous Silica-Based Support in Size Exclusion The fluorosurfactant-treated fluorosilane-coated porous silica-based column of this invention as in Example 1A, above, and a control Zorbax® BioSeries (a registered trademark of E. I. du Pont de Nemours & Co.) GF 450 gel filtration column packed with PSM 300 silica were used to perform size exclusion chromatography. A mobile phase of 0.2M sodium dihydrogen phosphate (SDHP), pH 7.0 adjusted with 2M sodium hydroxide, was pumped through each column at a flow rate of 1.0 mL/min. Two samples containing a mixture of various molecular weight marker proteins were prepared. One sample contained a mixture of thyroglobulin, IgG, bovine serum albumin (BSA), ovalbumin and lysozyme. The other sample contained a mixture of thyroglobulin, IgG, BSA, ovalbumin and myoglobin. Each sample also contained sodium azide, a low molecular weight permeation marker. An aliquot of each sample was run on the fluorosilane-coated porous silica-based column and the Zorbax ® Bioseries GF 450 gel filtration column.

The size exclusion distribution coefficient, $K_d$, was calculated for each of the marker proteins from the retention volume of each protein according to the following equation:

$$K_d = (V_r - V_o)/(V_m - V_o)$$

where
$V_r$ = retention volume of protein
$V_m$ = total permeation volume of the column
$V_o$ = total exclusion volume of the column.

A calibration curve was constructed for each column from a plot of the logarithm of marker protein molecular weight versus Kd value. The results showed that all of the marker proteins eluted at the volumes expected, demonstrating that none was retained by adsorption. Table 1, below, demonstrates the $K_d$ values of the marker proteins determined from the fluorosilane-coated porous silica-based column of this invention and those from the control Zorbax ® BioSeries GF 450 gel filtration column.

TABLE 1

$K_d$ VALUES OF MARKER PROTEINS

| MARKERS | MOLECULAR WEIGHT | $K_d$ HDF-SILANE COATED POROUS SILICA | GF450 |
|---|---|---|---|
| Thyroglobulin | 669,000 | 0.20 | 0.16 |
| IGG | 150,000 | 0.35 | 0.57 |
| BSA | 68,000 | 0.47 | 0.61 |
| Ovalbumin | 44,000 | 0.52 | 0.69 |
| Myoglobin | 17,500 | 0.59 | 0.85 |
| Lysozyme | 14,000 | 0.65 | 1.00 |
| Sodium Azide | 67 | 1.00 | 1.00 |

Nonspecific binding of lysozyme commonly observed with silica-based packings was significant on the GF 450 column as can be seen from the $K_d$ value of 1.0. Because of the fluorosurfactant coating on the fluorosilane-coated silica, the fluorosurfactant-treated fluorosilane-coated porous silica-based column of this invention did not exhibit significant retention of lysozyme. From the range of $K_d$ values, it can be concluded that the effective pore sizes of the packing materials of the fluorosurfactant-treated fluorosilane-coated porous silica-based column are smaller than those of GF 450 column packing materials. The small effective pore sizes can most likely be attributed to the fluorosurfactant coating on the fluorosilane-coated silica.

C. Determination of Desorption of Fluorosurfactant from the Fluorosilane Interlayer of Fluorosurfactant-Treated Fluorosilane-Coated Silica One would expect that the desorption of fluorosurfactant from the fluorosilane interlayer of a fluorosurfactant-treated fluorosilane-coated porous silica-based column would result in an increase in the retention of marker proteins on the column. Desorption of fluorosurfactant would increase the effective pore diameter and volume, enabling proteins to penetrate a greater number of pores, and would expose more surface area of the fluorosilane interlayer, increasing the amount of non-specific binding of proteins to the fluorosilane interlayer. To test the amount of desorption of fluorosurfactant from the fluorosurfactant-treated fluorosilane-coated porous silica-based column of this invention, the fluorosurfactant-treated fluorosilane-coated porous silica-based column prepared in Example 1A was operated continuously for 150 hours under the conditions set forth in Example 1B, above. The increase in effective pore diameter and volume was measured by the increase in retention of sodium azide. Table 2, below, summarizes the changes in the elution volumes of each marker as a function of time.

TABLE 2

ELUTION VOLUME CHANGES

| MARKERS | ELUTION VOLUME, ML | | | | % CHANGE |
|---|---|---|---|---|---|
| | HOUR 0 | HOUR 50 | HOUR 100 | HOUR 150 | |
| Thyroglobulin | 7.53 | 7.56 | 7.56 | 7.61 | 1.1 |
| IgG | 8.19 | 8.25 | 8.27 | 8.34 | 1.8 |
| BSA | 8.69 | 8.74 | 8.77 | 8.87 | 2.1 |
| Ovalbumin | 8.93 | 9.00 | 9.00 | 9.10 | 1.9 |
| Myoglobin | 9.27 | 9.33 | 9.37 | 9.50 | 2.5 |
| Lysozyme | 9.51 | 9.60 | 9.67 | 9.70 | 2.0 |
| Sodium azide | 11.02 | 11.03 | 11.03 | 11.13 | 1.0 |

There was no significant increase in the retention of the marker proteins after 150 hours of continuous column operation. Therefore, it can be concluded that there was no significant desorption of fluorosurfactant from the fluorosurfactant-treated fluorosilane-coated porous silica-based column of this invention. The results in Table 2 indicate that the retention of most of the marker proteins increased less than 2%. The sodium azide result indicates that a 1% change was due to increased effective pore diameter. The other 1% was probably due to increased nonspecific binding. The more hydrophobic proteins, such as BSA and myoglobin, showed a slightly greater than 2% increase in retention. Such increased retention is believed to have been caused by a weak reversed phase interaction between the protein and the fluorocarbon bonded phase of the fluorosilane interlayer.

EXAMPLE 2

Use of a Fluorosurfactant-Treated Fluorosilane-Coated Porous Silica-Based Support in Ion Exchange Chromatography Porous silica coated with fluorosilane prepared as in paragraph 1 of Example 1A was packed into a 8×0.62 cm stainless steel column by a standard packing procedure. The column was flushed with water and then treated with a solution of 0.5% Zonyl ® FSN and 0.4% Zonyl® FSC fluorosurfactants for 16 hours at a flow rate of 0.5 mL/min. This column was used for anion exchange separation of adenosine monophosphate (AMP), adenosine diphosphate (ADP) and adenosine triphosphate (ATP) with a sodium chloride gradient of 0–1M sodium chloride in 10 mM TRIS buffer, pH 8.0. The gradient elution was complete in 30 minutes. The same column and experimental conditions were used to separate myoglobin, ovalbumin and carbonic anhydrase. Acceptable separation of all compounds was achieved with the fluorosurfactant-treated fluorosilane-coated porous silica-based column of this invention.

EXAMPLE 3

Use of a Fluorosurfactant-treated Fluorosilane-Coated Porous Silica-Based Support in Protein a Affinity Column Chromatography Fifty grams Zorbax ® PSM 1000, having an average pore diameter of 1000 angstroms and coated with zirconium according to U.S. Pat. No. 4,600,646, was coated with the fluorosilane as described in the first paragraph of Example 1A. The fluorosilane-coated silica thus prepared was packed into a 5×0.46 cm stainless steel column by a standard packing procedure. The column was washed with 20 mL THF followed by 20 mL water at a flow rate of 1 mL/min.

Protein A was perfluoroalkylated by dissolving 100 mg of a recombinant modified Protein A (expressed in *E. coli* and lacking C-terminal domain, obtained from Porton Products Ltd., U.K.) in 100 mL of 0.10 M phosphate buffer, pH 8.5 (PB). Next, 19.6 mL of a 0.05% (v/v) solution of perfluorooctylpropyl isocyanate in dioxane was added to 98.0 mL of the modified Protein A solution. The reaction mixture was mixed gently and allowed to react for 7 hours at room temperature and then overnight at 4° C. The reaction mixture was then centrifuged at 3,000 rpm for 5 min. to remove any denatured protein or other insoluble reaction by-products.

The degree of substitution of modified Protein A by the isocyanate was determined by determining the remaining available amino groups by standard procedures using trinitrobenzene sulfonic acid. The amount of substitution was calculated from the difference in the amount of available amino groups between a control (no isocyanate treatment) and the isocyanate-treated modified Protein A. The average number of amino groups reacted on the modified Protein A molecule was found to be 4.

A 20-mL solution a 1:1 dilution of the perfluoroalkylated modified Protein A with PB was split into two aliquots. Each aliquot was pumped through the column to allow immobilization of the perfluoroalkylated modified Protein A. The column was then washed with 0.2% Zonyl ® FSN until no more perfluoroalkylated modified Protein A was removed as determined by the UV absorption monitoring of the column effluent at 280 nm. The amount of perfluoroalkylated modified Protein A in the effluent fractions was determined. A total of 12.2 mg of perfluoroalkylated modified Protein A was washed from the column, leaving 7.8 mg of perfluoroalkylated modified Protein A immobilized on the column.

Binding capacity of the affinity column was evaluated using human IgG at different loading levels. The column was equilibrated in 0.1M sodium phosphate buffer, pH 8.0, 0.02% sodium azide. Five, ten, fifteen and twenty milliliters of a 1 mg/mL solution of human IgG in equilibration buffer were injected into the column. The column was washed with the same buffer for at least 4 column volumes before the bound IgG was eluted using 0.1M glycine, pH 3.0. At the maximum load level, binding capacity was 14 mg of IgG which corresponds to approximately 28 mg of IgG per gram of packing material. Binding capacities for previously described solid perfluorocarbon-based columns have been determined to be about 7 mg of IgG (Applicants' assignee's, E. I. du Pont de Nemours & Company, Ser. No. 07/134,028, filed Dec. 17, 1987). Therefore, the fluorosilane-coated porous silica-based support of this invention has a much greater binding capicity than previously described solid perfluorocarbon-based supports.

EXAMPLE 4

Enzyme Immobilization onto a Preactivated Fluorosilane-Coated Porous Silica Carrier Core A modified reactive perfluorocarbon anchor compound containing a spacer group was prepared by dissolving 1.0 gram of 1,4-butanediol diglycidyl ether in 4 mL of dioxane; slowly adding 0.5 gram of perfluorohexylpropyl amine to the rapidly stirring ether solution; and stirring the resulting mixture for approximately 12 hours at room temperature.

A 0.5-gram sample of flourosilane-coated silica, prepared as described in paragraph 1 of Example 1A, was washed once with 5 mL of methanol, followed by two washes with 5 mL of dioxane per wash. The washed fluorosilane-coated silica was preactivated by adding to it 5 mL of the modified reactive perfluorocarbon anchor compound mixture, followed by 25 mL of deionized water. The resulting suspension was stirred for 30 minutes at room temperature and the preactivated fluorosilane-coated silica was washed six times with 5 mL of deionized water per wash.

To the preactivated fluorosilane-coated silica was added 5 mL of a polynucleotide phosphorylase solution containing 3.59 mg of enzyme per mL of 0.1M, pH 6.0 2-(N-morpholino)ethanesulfonic acid (MES) buffer. The resulting suspension was stirred for approximately 12 hours at room temperature to immobilize the enzyme. The preactivated fluorosilane-coated silica with immobilized enzyme was washed three times with 5 mL of MES buffer per wash. The amount of enzyme immobilized onto the preactivated fluorosilane-coated silica was determined to be 12.6 mg/g using a spectrophotometric protein assay to measure the protein remaining in the enzyme solution and in the wash solutions.

The activity of the immobilized polynucleotide phosphorylase was determined by measuring the amount of phosphate released from the enzyme catalyzed polymerization of adenosine diphosphate (ADP). Fifty microliters of the preactivated fluorosilane-coated silica with immobilized enzyme was added to 80 $\mu$L of a reaction mixture containing 50 mM $MgCl_2$, 0.4 mM EDTA, and 20 mM ADP in 0.1 M Tris buffer, pH 9.0. The enzyme was allowed to react for 15 minutes at 37° C. The reaction was quenched with 0.9 mL of 2.5% perchloric acid. The mixture was cooled to 0° C. in an ice bath for 10 minutes and then centrifuged for 3 minutes. The supernatant was mixed with 1.2 mL of a solution containing 10.98 g of zinc acetate and 9.27 g of ammonium molybdate per 500 mL of deionized water and adjusted to pH 5.0. The resulting solution was mixed vigorously and allowed to stand for 1 minute. The absorbance of the solution was measured at 350 nm to determine the phosphate concentration. The preactivated fluorosilane-coated silica with immobilized enzyme was washed several times with deionized water, dried at 110° C., and weighed to determine the dry weight of the silica used in the assay. The immobilized activity was found to be 0.5 Unit per gram of support (defined as the number of μmoles of ADP polymerized, as measured by phosphate release, in 15 minutes at 37° C.). Therefore, enzymes can be successfully immobilized on the preactivated fluorosilane-coated porous silica carrier cores of this invention.

We claim:

1. A solid support containing an attached ligand or binder for the ligand consisting essentially of:
   (A) a non-perfluorocarbon solid carrier core;
   (B) a fluorocarbon layer coated on said solid carrier core;
   (C) a ligand or binder for the ligand securely but reversibly attached to the surface of said fluorocarbon layer through a reactive perfluorocarbon anchor compound; and
   (D) a nonionic fluorosurfactant coating on said fluorocarbon layer.

2. The support of claim 1, wherein said carrier core is selected from the group consisting of silica, magnetic particles, polystyrene, polypropylene and polyethylene.

3. The support of claim 1, wherein said fluorocarbon layer is fluorosilane.

4. An ion-exchange chromatographic solid support consisting essentially of:
   (A) a non-perfluorocarbon solid carrier core;
   (B) a fluorocarbon layer coated on said solid carrier core;
   (C) a cationic fluorosurfactant securely but reversibly attached to the surface of said fluorocarbon layer; and
   (D) a nonionic fluorosurfactant coating on said fluorocarbon layer.

5. A process of preparing a solid support containing an attached ligand or binder for the ligand comprising the steps of:
   (A) contacting a non-perfluorocarbon solid carrier core with a fluorocarbon compound to form a fluorocarbon layer on said solid carrier core;
   (B) modifying a ligand or binder for the ligand by attaching a reactive perfluorocarbon anchor compound to said ligand or binder for the ligand;
   (C) contacting said fluorocarbon layer on said solid carrier core with said perfluorocarbon-substituted ligand or binder for the ligand to attach the ligand or binder to the surface of said fluorocarbon layer through said reactive perfluorocarbon anchor compound; and
   (D) contacting said fluorocarbon layer with a nonionic fluorosurfactant.

6. A process of preparing a solid support containing an attached ligand or binder for the ligand comprising the steps of:
   (A) contacting a non-perfluorocarbon solid carrier core with a fluorocarbon compound to form a fluorocarbon layer on said solid carrier core;
   (B) preactivating said fluorocarbon layer on said solid carrier core by attaching a reactive perfluorocarbon anchor compound to said fluorocarbon layer;
   (C) contacting said preactivated fluorocarbon layer on said solid carrier core with a ligand or binder for the ligand to attach said ligand or binder to the surface of said preactivated fluorocarbon layer through said reactive perfluorocarbon anchor compound; and
   (D) contacting said preactivated fluorocarbon layer with a nonionic fluorosurfactant.

7. The process of claim 6, wherein said reactive perfluorocarbon anchor compound contains a spacer group between a reactive group and an anchor portion of said reactive perfluorcarbon anchor compound.

8. The process of claim 7, wherein said spacer group is selected from the group consisting of derivatives of polylysine, polyglutamic hydrazide, polyacrylic hydrazide, hexamethylene diamine and 6-aminocaproic acid.

9. The process of claim wherein said spacer group is a derivative of ethylene glycol.

10. A bioaffinity separation process comprising the steps of:
    (A) forming a solid affinity support by
       (a) attaching a ligand or a binder for the ligand to the surface of a fluorocarbon layer coated on a non-perfluorocarbon solid carrier core through a reactive perfluorocarbon anchor compound; and
       (b) contacting the product of step (a) with a nonionic fluorosurfactant to form an affinity support; and
    (B) capturing a binder or ligand, complementary to the ligand or binder attached to said fluorocarbon layer from a mixture using said solid affinity support.

11. An immobilized enzyme system consisting essentially of:
    (A) a non-perfluorocarbon solid carrier core;
    (B) a fluorocarbon layer coated on said solid carrier core;
    (C) an enzyme attached securely but reversibly to the surface of said fluorocarbon layer through a reactive perfluorocarbon anchor compound; and
    (D) a nonionic fluorosurfactant coating on said fluorocarbon layer.

* * * * *